United States Patent [19]

Ring

[11] Patent Number: 4,727,037
[45] Date of Patent: Feb. 23, 1988

[54] ASSAY KIT AND METHOD FOR THE DETERMINATION OF ANTIBODY CLASS AND SUBCLASS

[75] Inventor: David B. Ring, Redwood City, Calif.

[73] Assignee: Cetus Corporation, Emeryville, Calif.

[21] Appl. No.: 580,519

[22] Filed: Feb. 15, 1984

[51] Int. Cl.$^4$ .................. G01N 33/53; G01N 33/543; G01N 33/577
[52] U.S. Cl. ......................................... 436/548; 435/7; 435/240.26; 435/805; 435/810; 436/513; 436/530; 436/808; 436/809; 436/810; 935/103; 935/110
[58] Field of Search ............... 436/548, 513, 501, 530, 436/808, 809, 810, 518; 435/7, 805, 810, 240.26; 422/56, 57, 61

[56] References Cited

U.S. PATENT DOCUMENTS

| | | | |
|---|---|---|---|
| 4,002,532 | 1/1977 | Weltman et al. | 195/103.5 A |
| 4,216,245 | 8/1980 | Johnson | 427/2 |
| 4,273,756 | 6/1981 | Ling et al. | 424/1 |
| 4,347,311 | 8/1982 | Schmitz | 435/5 |
| 4,434,227 | 2/1984 | Unger | 435/7 |
| 4,591,570 | 5/1986 | Chang | 436/518 |

OTHER PUBLICATIONS

McDougal, J. S.; Browning, S. W.; Kennedy, S. and Moore, D. D., *Journal of Immunological Methods*, 63, 281–290 (1983).

Beyer, D. F., *Journal of Immunological Methods*, 67, 79–87 (1984).

Bennett, F. C. and Yeoman, L. C., *Journal of Immunological Methods*, 61, 201–207 (1983).

Hawkes, R., Niday, E. and Gordon, J., *Analytical Biochemistry*, 119, 142–147 (1982).

Herbrink, P., Van Bussel, F. J. and Warnaar, S. O., *Journal of Immunological Methods*, 48, 293–298 (1982).

Horejsi, V. and Hilgert, I., *Journal of Immunological Methods*, 62, 325–329 (1983).

Huet, J., Sentenac, A. and Fromageot, P., *Journal of Biological Chemistry*, 257 (5), 2613–2618 (1982).

Menard, S., Tagliabue, E., Canevari, S., Fossati, G. and Colnaghi, M. I., *Cancer Research*, 43, 1295–1300 (1983).

Scheinberg, D. A., Pan, X. Q., Wilsnack, R. and Strand, M., *Journal of Immunological Methods*, 58, 285–292 (1983).

Wagener, C., Yang, Y. H., Crawford, F. G. and Shively, J. E., *Journal of Immunology*, 130, 2308–2315 (1983).

*Primary Examiner*—Sidney Marantz
*Attorney, Agent, or Firm*—Leona L. Lauder; Linda J. Nyari; Albert P. Halluin

[57] ABSTRACT

A method of rapid determination of the isotype class for a panel of monoclonal antibodies is described. The assay comprises adsorbing on a solid support medium antibodies directed to specific immunoglobulin heavy and light chains. Once such isotype-specific antibodies are bound to the nitrocellulose paper, the treated strips can be incubated with the monoclonal antibody of interest. Upon formation of a complex between the specific isotype antisera and the monoclonal antibody, the complex is visualized by reaction with a chromogenic substance. In the preferred embodiment of the invention, the treated nitrocellulose strips are stored in kit form. Using these prepared strips, the isotyping assay can be performed in less than two hours with a minimum of technical manipulation and expenditure of reagents.

15 Claims, 2 Drawing Figures

ASSAY KIT AND METHOD FOR THE DETERMINATION OF ANTIBODY CLASS AND SUBCLASS

FIELD OF THE INVENTION

This invention relates to the method for determining the isotype class and subclass for a panel of monoclonal antibodies. More specifically it relates to a test kit comprising a solid phase carrier to which is bound isotype specific antisera capable of binding to a monoclonal antibody based on its particular immunoglobulin class.

BACKGROUND OF THE INVENTION

Isotype is a property of an antibody referring to those antigenic determinants that characterize the heavy and light chains of the immunoglobulin molecule into specific classes and subclasses. Isotype-specific antisera are prepared by immunizing an animal of one species with antibodies of a single immunoglobulin class from another species and then affinity purifying the resulting immune serum by adsorption against antibodies of the other classes to remove all components except those specific for the immunizing class.

The five immunoglobulin classes are distinguished structurally by differences in their heavy chain constant region. There are five major heavy chain classes, designated $\alpha$, $\gamma$, $\delta$, $\epsilon$ and $\mu$. These heavy chain classes define the corresponding immunoglobulin classes IgA, IgG, IgD, IgE and IgM respectively. Some classes are divided into subclasses thereby indicating heavy chain constant regions which are distinct and closely related in their amino acid sequence. In the mouse the IgG class has subclasses $\gamma 1$, $\gamma 2a$, $\gamma 2b$ and $\gamma 3$.

In addition to the class and subclasses defining the constant heavy chain region, there is also a classification based on the constant light chain region which is defined by comparisons in amino acid sequence. The classes defining the different light chains are classified as either $\kappa$ or $\lambda$ light chain. As with the heavy chain classifications, knowledge of the class aids in defining specific properties and physiological functions of the immunoglobulin molecule.

A knowledge of the isotype class and subclass of an antibody is necessary in order to more fully utilize the biochemical characteristics of a particular antibody. Characterization of a particular monoclonal antibody into its class and subclass serves as an additional means to identify the type of monoclonal antibody being produced by the hybridoma cell. In addition, knowledge of the immunoglobulin class aids in the development of purification schemes for the monoclonal antibody based on the particular physical and biochemical properties of its subclass. By utilizing specific properties of the antibody which are characteristic of the individual class, the ideal antibody can be chosen for use in specific immunologic assays.

When designing specific immunoassays or therapeutic applications of antibodies the different characteristics based on class can be exploited. There has been data reported which shows that IgG2a antibodies have more effect than the other subclasses in stimulating cellular immune response and as such may be useful in therapeutic studies. Certain IgM antibodies in addition to the IgG antibodies have been found to be good immunotoxins having an effect on immunotoxin action and biodistribution. In addition, certain subclasses have been found to be effective in initiating the complement reaction. On the other hand, some mouse IgG3 and IgM antibodies have a tendency to precipitate out of solution and may therefore be unacceptable in many immunologic assays.

Determination of heavy and light chain isotypes is frequently used in the characterization of monoclonal antibodies; therefore, a variety of assays for the determination of light and heavy chain isotypes have been developed. The classical method for isotyping is known as Ouchterlony radial immunodiffusion wherein the solution containing the monoclonal antibody is placed in a round center well cut from an agarose base and isotype antisera are placed in surrounding wells in a hexagonal configuration. The antigen-antibody reaction is then noted by visible immunoprecipitin bands at the point of reactivity. This procedure, however, it slow and requires relatively large amounts of isotype-specific antisera. Another isotyping method is based on initial adsorption of monoclonal antibody to a solid phase antigen preparation. In this technique the immobilized antibody is then probed with radiolabeled isotype specific antisera or with unlabeled isotype-specific antisera followed by a radio-labeled or enzyme-tagged second antibody (Wagener, C. et al., 1983, *J. Immunol.* 130, 2308; Menard, S. et al., 1983, *Cancer Research*, 43, 1295).

An improvement on the use of the enzyme immunoassays (EIA) has recently been published (Bennett, F. et al., 1983, *J. Immunol. Methods*, 61, 201). In that article, the use of a dot immuno binding assay is described wherein up to ninety-six assays can be performed utilizing a single nitrocellulose sheet. A subsequent article (Horejsi, V. et al., 1983, *J. Immunol. Methods*, 62, 325.) describes the use of nitrocellulose membranes as carriers of antigen for rapid screening of specific monoclonal antibodies or as carriers of the monoclonal antibody for a determination of isotype. In all the referenced articles the antigen or monoclonal antibody is immobilized on a solid support whereon the EIA is performed. By binding the antigen or monoclonal antibody to the nitrocellulose paper first, numerous wash steps and additional reagents are necessary to achieve an accurate determination of the immunoglobulin class. Furthermore, it is often difficult to obtain suitable antigen in good quantity or to immobilize it successfully. The use of a specific antigen limits the generality of any isotype assay in which antigen immobilization is the initial step, since different antigens will be required if monoclonal antibodies of different specificity are to be tested.

Recently a method for detecting antibodies by means of reacting the antibody with antigen that has been spotted onto nitrocellose paper has been described (Herbrink, P. et al., 1982, *J. Immunol. Methods*, 48, 293). The antigen spot test is a highly sensitive assay for the detection of antibodies by utilizing a modification of the commonly used radioimmunoassay (RIA) and enzyme linked immunosorbent assay (ELISA). By spotting the antigen on the nitrocellulose paper the quantity of antigen required is reduced; however, a source of purified antigen directed to the monoclonal antibody of interest is still required in order to perform this assay. The method of Herbrink et al. does, however, provide a means of spotting onto nitrocellulose paper the various antigens thereby enabling the screening of numerous samples in a single assay. Bound antibodies are detected by incubating the paper containing the complex with either $^{125}$I-labeled protein A or using a second antibody conjugated to horseradish peroxidase. While the Herbrink, et al. paper does not teach the development of a method for isotype determination, it does serve as useful background information in the step-by-step development of successful immunologic assays based on the adsorption of an antigen-antibody complex onto a solid support.

Prior to the instant invention, the typing of monoclonal antibodies has required specific antigen and relatively large quantities of isotype specific antisera. The instant invention eliminates the need for specific antigen completely and is designed to be a rapid yet accurate method for determining isotype class without resorting to a multiplicity of steps or need for microtitration trays requiring numerous technical manipulations. By eliminating the need for specific antigen, a panel of monoclonal antibodies can be rapidly and accurately typed by using a solid support medium such as nitrocellulose strips with the adsorbed isotype antisera. When this probe is dipped in an antibody containing solution, e.g., spent hybridoma culture supernatant or mouse ascites fluid, then developed using a chromogenic substrate, the result is a visually detectable spot at the corresponding class and subclass for the specific antibody being tested.

SUMMARY OF THE INVENTION

One embodiment of the present invention relates to the formation of an isotyping kit comprising of a solid support medium upon which is bonded specific isotype antisera in a predetermined spatial arrangement, blocking buffer and a chromogenic substrate. Once antisera has been bound to the support, the blocking buffer is introduced to eliminate any non-specific binding of the monoclonal antibody of interest. Upon formation of a complex between the specific isotype antisera and the monoclonal antibody, the chromogenic substrate is used to visualize the complex so formed. In the preferred embodiment of the invention, the solid support medium upon which the reaction takes place is nitrocellulose paper.

Another embodiment of the invention relates to a method for determining the immunoglobulin class or subclass of an antibody test solution whereby a panel of monoclonal antibodies can be rapidly tested. By adsorbing onto a solid support medium having been bonded thereto in a predetermined spatial arrangement antisera directed to isotype class and subclass, test fluid containing the antibody of interest can be reacted with the adsorbed antisera so as to form a complex which can then be visualized by the addition of a chromogenic substrate.

By the use of pre-tested solid support medium such as nitrocellulose strips, the typing reaction can be completed in less than two hours and with the use of as little as 50 $\mu$l of test antibody. The rapidity of the assay coupled with the reproducibility of results achieved while expending only small quantities of reagents makes this technique an ideal method for the screening of panels of monoclonal antibodies.

DETAILED DESCRIPTION OF THE DRAWINGS

Figure 1:
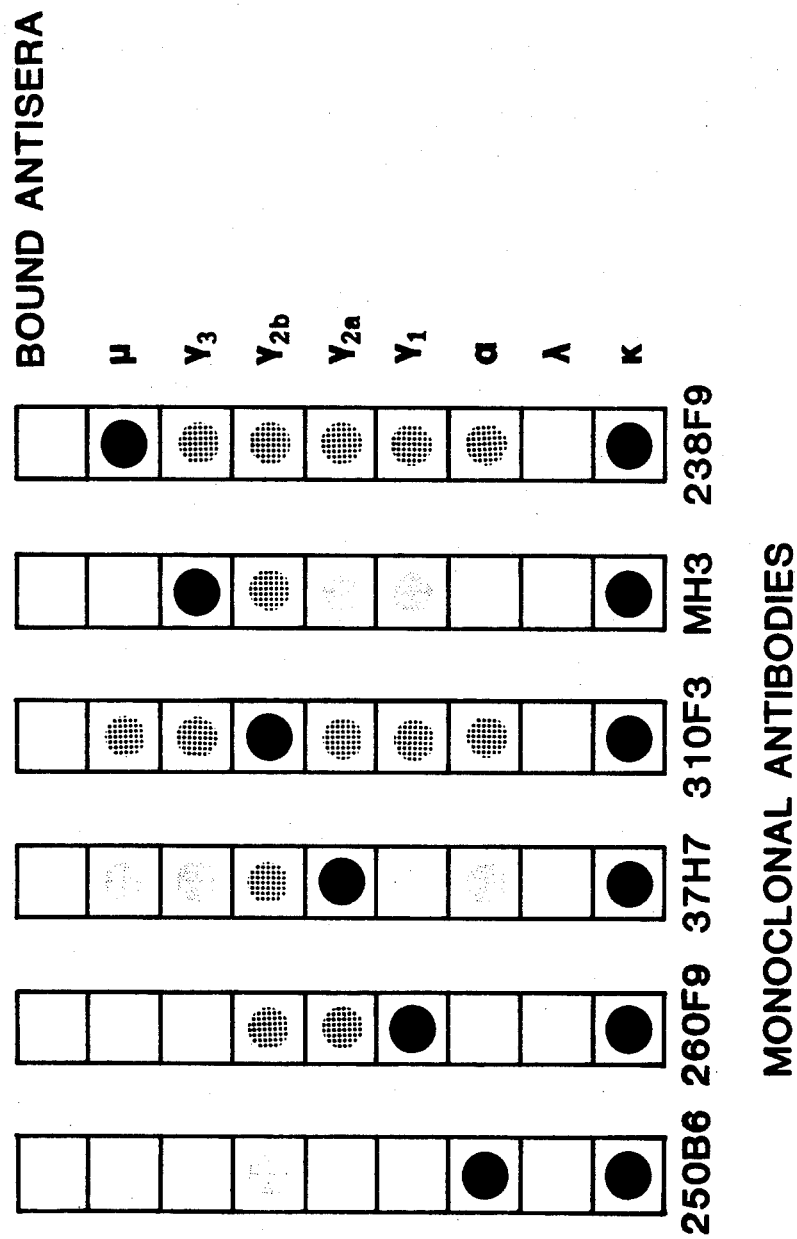

FIG. 1 is a graphic illustration of results obtained when a panel of monoclonal antibodies was screened for isotype classification. Each strip is representative of actual results obtained when the prepared nitrocellulose strip containing isotype antisera for each mouse heavy and light chain class is reacted with a monoclonal antibody. A positive reaction is indicated by an intense spot at the point of reactivity. The lighter spots result from cross reactivity in the isotype antisera used to make the probe, and will vary depending on how well specific lots of such antisera have been affinity purified by the manufacturer. In no instance, however, are the cross-reactions of such intensity that a false positive is obtained. Despite the potential cross-reactivity of the isotype antisera, a check using known isotyping methods verified the reproducibility and accuracy of this method.

Figure 2:
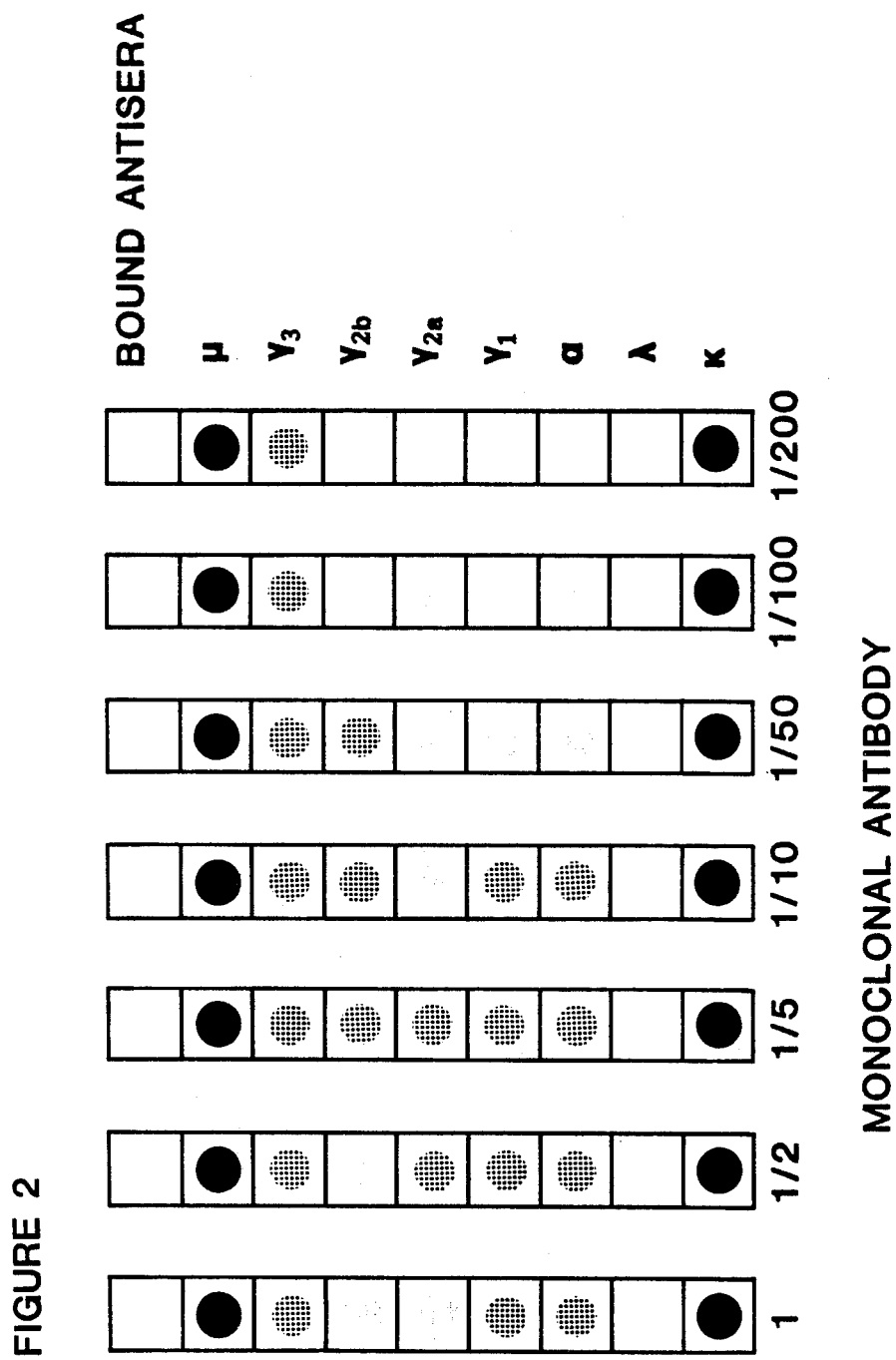

FIG. 2 is a similar illustration of the degree of sensitivity which can be obtained using the described method of isotype determination. As indicated, it is possible to use very dilute solutions containing the monoclonal antibody of interest and still obtain reproducible results. As shown in the figure, the use of a dilute preparation acts to reduce the degree of cross-reaction due to the impure preparation of isotype antisera.

DETAILED DESCRIPTION OF THE INVENTION

The present invention includes a method for determining the isotype of a panel of monoclonal antibodies which comprises adsorbing on a solid support medium antibodies directed to specific immunoglobulin heavy and light chains. Once such isotype-specific antisera are bound to the solid support medium they can be stored until desired for use. The solid support medium upon being treated with the isotype specific antisera is incubated with antibody present in, for example, spent hybridoma culture fluid or mouse ascites fluid. After the complex has been formed, the specific immunoglobulin heavy and light chain can be determined visually by reacting the complex with a chromogenic substrate.

By the method described herein it is possible to rapidly classify the immunoglobulin as to isotype by reacting the monoclonal antibody of interest with isotype specific antisera adsorbed to a solid support medium which may include for example, nitrocellulose paper or diazo paper. By reacting the isotype specific antisera directly onto the nitrocellulose paper, the need for specific antigen is eliminated. Such an improvement thereby enables the typing of an unlimited number of monoclonal antibodies without requiring specific antigen corresponding to each monoclonal antibody of interest. In addition, direct binding of the isotype antisera acts to greatly increase the rapidity and reproducibility of the assay. Since the antisera being bound is commercially available and will be the same for each strip prepared, a high degree of quality control can be enforced and the resulting prepared strip is suitable for use in kit form.

A source of the monoclonal antibody may be, for example, spent hybridoma culture supernatant or mouse ascites fluid. The paper containing the adsorbed antisera is successively incubated with the solution containing the antibody of interest, an enzyme-tagged second antibody, such antibody derived from the same species as the monoclonal antibody of interest so as to prevent cross-reaction, and a chromogenic substrate solution. The chromogenic substrate reaction enables one to identify the heavy and light chain of each monoclonal antibody by observing dots that turn dark.

In a preferred embodiment of the invention nitrocellulose paper already spotted with class specific antisera is used. Once the class specific antisera has been adsorbed to the nitrocellulose paper the paper may be stored dry or in buffer until needed. When such pretreated strips are used, the entire isotyping procedure can be accomplished in two hours and with less than one milliliter of monoclonal antibody containing solution.

In the instant invention, the term "solid support medium" is meant to include any solid substance capable of binding antisera of interest. Non-limiting examples of this type of solid substance include nitrocellulose paper and diazo paper. The type of "blocking buffer" required may differ depending on the solid support medium used, however, it will be of the type, for example, bovine serum albumin in a tris buffer or water solution, capable of blocking any unreactive sites on the paper and thereby preventing non-specific binding. In order to visualize the complex formed, a chromogenic substrate is required. In the preferred embodiment of the invention, the "chromogenic substrate" is for example a peroxidase conjugated second antibody developed in 0.03% 3,3 diamino benzidine and 0.05% hydrogen peroxide.

Binding of the specific isotype antisera in a "predetermined spatial arrangement" onto the solid support medium is an important feature of the instant invention in that it allows for the rapid identification of the specific isotype class for a given monoclonal. By adsorbing the isotype antisera onto the solid support medium at a pre-defined position, the method lends itself to development as a rapid assay kit. The specific class or subclass for the monoclonal antibody of interest can immediately be identified by its position on the solid support medium.

In one embodiment of the invention, the solid support medium comprised of nitrocellulose strips are strips prepared and stored in kit form representing all of the mouse immunological classes and subclasses. When prepared in this form the actual time required to carry out the isotyping assay for a given monoclonal antibody is less than two hours and as little as 0.25 µg of each isotype antisera has been utilized. The rapidity with which the assay can be completed and the small amount of reagent required result in this invention having considerable advantages over known methods.

The following examples are offered by way of illustration and are not intended to limit the invention in any manner.

EXAMPLE I

A grid of 5 mm squares was drawn in pencil on a nitrocellulose sheet (Bio Rad Laboratories). One microliter drops of rabbit isotype antisera were spotted onto the grid squares so that each one by eight array of squares contained one spot of each light and heavy chain reagent in a predetermined spatial arrangement. Rabbit antisera to mouse kappa, lambda, alpha, gamma 1, gamma 2a, gamma 2b; gamma 3 and mu immunoglobulin chains were obtained from Litton Bionetics. The nitrocellulose sheet containing the specific isotype antisera was then incubated one hour at room temperature in a moist chamber, rinsed with 0.01M phosphate, 0.15M NaCl pH 7.2 (PBS), 1% bovine serum albumin (BSA) and left overnight in PBS/BSA at 4° C. The nitrocellulose strips must be incubated with PBS/BSA after reaction with the antisera in order to prevent non-specific binding at the unreacted sites on the strip. The nitrocellulose strip as prepared was incubated in 3 ml of spent hybridoma culture supernatant or mouse ascites fluid containing the monoclonal antibody of interest, rinsed three times with PBS/BSA followed by incubation for one hour in a 1:200 dilution of commercially available rabbit antimouse peroxidase diluted in PBS/BSA. Depending on the size of the nitrocellulose strip used, as little as 50 µl of supernatant can be used in the analysis. After rinsing two times in PBS/BSA followed by two rinses in 50 mM tris pH 7.6 (tris buffer) the reactive strip was incubated in 50 mM tris buffer containing 0.03%, 3.3 diaminobenzidine (Sigma Chemical Co.) and 0.05% hydrogen peroxide in tris buffer according to the method of Bennet, F. et al., 1983, *J. Immunol. Methods*, 61, 201. Within three to four minutes after reacting with the peroxide substrate sufficient color developed to determine the isotype for each monoclonal antibody tested.

The instant invention was tested on twenty-one mouse monoclonal antibodies representing six immunoglobulin heavy chain classes. The isotyping method described is not limited to the typing of mouse monoclonal antibodies alone. Provided the class specific isotype antisera is available, monoclonal antibodies of other species, such as human monoclonal antibodies, can be typed using this method. FIG. 1 gives a graphic illustration of the results using mouse monoclonal antibodies. To check the accuracy and specificity of this testing method, the twenty-one mouse monoclonal antibodies were also typed using a commercial EIA kit (obtained from Zymed) following their instructions for use. Additionally, sixteen of the twenty-one mouse monoclonal antibodies were endogenously labeled with $^{35}$S-methionine and electrophoresed on sodium dodecyl sulfate (SDS) polyacrylamide gels for determination of heavy chain molecular weight. Table I compares the results of the three assay methods. As indicated by the table, the nitrocellulose strip method described herein provides a reproducible and highly accurate means for classifying antibodies as to their isotype.

TABLE I

Comparison of the results using the three different assay methods.

| ANTIBODY | STRIP | COMMERCIAL TYPING KIT | GROWTH LABEL |
|---|---|---|---|
| 42H8 | α | α | α |
| 250B6 | α | γ1 (+α) | α |
| 200F9 | γ1 | γ1 | γ |
| 245E7 | γ1 | γ1 | γ |
| 260F9 | γ1 | γ1 | γ |
| 317G5 | γ1 | γ1 | γ |
| 7G5 | γ1 | γ1 | ND |
| 37H7 | γ2a | γ2a | γ |
| 104F4 | γ2a | γ2a | γ |
| 7B3 | γ2a | γ2a | ND |
| 310F3 | γ2b | γ2b | γ |
| MA2 | γ2b | γ2b | ND |
| 44F4 | γ3 | γ3 | γ |
| 113F1 | γ3 | γ3 | γ |
| 274G6 | γ3 | γ3 | γ |
| MH3 | γ3 | γ3 | ND |
| MA1 | γ3 | γ3 | ND |
| 238F9 | mu | mu | mu |
| 239E3 | mu | mu | mu |
| 254H9 | mu | mu | mu |
| 263D11 | mu | mu | mu |

EXAMPLE II

Studies were performed (FIG. 2) using the nitrocellulose strip method in order to determine the sensitivity of the assay when using diluted hybridoma culture supernatants. Seven monoclonal antibodies were tested by diluting the culture supernatant from 1:1 to 1:200 final dilution in PBS/BSA. Using this method with isotype antisera directed against kappa light chain and mu heavy chain the diluted monoclonal antibodies gave visually readable results within approximately the same assay time as for the undiluted samples. The results as illustrated in FIG. 2 indicate the sensitivity of the assay as developed. In addition, dilution of the spent hybridoma culture supernatant or mouse ascites fluid greatly reduces the background due to impurities in the isotype antisera. These experiments also verified that an undiluted culture supernatant as used in Example I can be assayed with incubation times in monoclonal antibody and rabbit antimouse peroxidase reduced to thirty minutes with only minimal loss in the intensity of the signal.

Modifications of the methods described above that are obvious to those of ordinary skill in immunology and related sciences are intended to be within the scope of the following claims.

What is claimed is:

1. An isotyping kit comprising nitrocellulose paper or diazo paper to which isotype specific antisera are bonded in a predetermined spatial arrangement.

2. An isotyping kit which comprises: nitrocellulose paper or diazo paper upon which isotype specific antisera are bonded in a predetermined spatial arrangement; a vial containing an amount of blocking buffer sufficient to prevent non-specific binding to said nitrocellulose paper or diazo paper; a chromogenic substrate designed to detect the presence of antibodies bound to said isotype specific antisera.

3. An isotyping kit according to claim 1 or 2 wherein the isotype specific antisera are bonded to strips of nitrocellulose paper.

4. An isotyping kit according to claim 3 wherein said strips of nitrocellulose paper are preserved in buffer.

5. An isotyping kit according to claim 3 wherein said strips of nitrocellulose paper are packaged in dry form.

6. An isotyping kit according to claim 1 or 2 wherein said isotype antisera are directed to the specific class and subclasses of immunoglobulin heavy and light chains.

7. An isotyping kit according to claim 6 wherein said immunoglobulins have as their heavy chain subunit gamma, alpha or mu.

8. An isotyping kit according to claim 6 wherein said immunoglobulin heavy chains are mouse immunoglobulins of the subclasses gamma 1, gamma 2a, gamma 2b, and gamma 3.

9. An isotyping kit according to claim 6 wherein said immunoglobulin light chains are of the class kappa and lambda.

10. A method for determining the class and subclass of a test antibody which comprises:
  a. adsorbing on nitrocellulose paper or diazo paper in a predetermined spatial arrangement antisera directed to isotype class and subclasses of an immunoglobulin;
  b. contacting said adosrbed isotype specific antisera with a fluid containing a test antibody to form a complex between the specific immunoglobulin heavy and light chains of the adsorbed antisera and said test antibody present in the fluid; and
  c. reacting said complex so formed with a chromogenic substrate to thereby identify the specific class or subclass of said test antibody.

11. A method according to claim 10 wherein said class of immunoglobulins have as their heavy chain subunit gamma, alpha or mu.

12. A method according to claim 10 wherein said class of immunoglobulins is mouse immunoglobulins of the subclasses gamma 1, gamma 2a, gamma 2b, and gamma 3.

13. A method according to claim 10 wherein said class of immunoglobulins have as their light chain subunit kappa or lambda.

14. A method according to claim 10 wherein said antibody containing fluid is spent hybridoma culture supernatant.

15. A method according to claim 10 wherein said antibody containing fluid is mouse ascites fluid.

* * * * *